United States Patent
Mo et al.

(10) Patent No.: US 10,011,542 B2
(45) Date of Patent: Jul. 3, 2018

(54) METHODS OF MEASURING PH IN REFINERY STREAMS

(71) Applicant: BAKER HUGHES INCORPORATED, Houston, TX (US)

(72) Inventors: Hua Mo, Friendswood, TX (US); Roger D. Metzler, Sugar Land, TX (US)

(73) Assignee: Baker Hughes, a GE company, LLC, Houston, TX (US)

(*) Notice: Subject to any disclaimer, the term of this patent is extended or adjusted under 35 U.S.C. 154(b) by 103 days.

(21) Appl. No.: 15/135,202

(22) Filed: Apr. 21, 2016

(65) Prior Publication Data

US 2016/0311734 A1   Oct. 27, 2016

Related U.S. Application Data

(60) Provisional application No. 62/152,347, filed on Apr. 24, 2015.

(51) Int. Cl.
| | |
|---|---|
| *G01N 21/80* | (2006.01) |
| *G01N 21/78* | (2006.01) |
| *C10G 17/00* | (2006.01) |
| *C10G 19/00* | (2006.01) |
| *C07C 7/20* | (2006.01) |
| *G01N 21/64* | (2006.01) |

(52) U.S. Cl.
CPC ............. *C07C 7/20* (2013.01); *C10G 17/00* (2013.01); *C10G 19/00* (2013.01); *G01N 21/643* (2013.01); *G01N 21/80* (2013.01); *G01N 21/78* (2013.01); *Y10T 436/21* (2015.01)

(58) Field of Classification Search
CPC .......... C07C 7/20; C10G 17/00; C10G 19/00; G01N 21/64; G01N 21/643; G01N 21/78; G01N 21/80; Y10T 436/21
USPC ..... 436/139, 147, 163, 164, 172; 422/82.05, 422/82.08, 82.09, 82.12
See application file for complete search history.

(56) References Cited

U.S. PATENT DOCUMENTS

| | | | | |
|---|---|---|---|---|
| 4,200,110 | A * | 4/1980 | Peterson | A61B 5/14539 356/39 |
| 2004/0087031 | A1 * | 5/2004 | Simon, Jr. | G01N 27/4167 436/100 |
| 2010/0108566 | A1 * | 5/2010 | Scattergood | C10G 7/10 208/47 |
| 2012/0142115 | A1 * | 6/2012 | Banks | G01N 21/6428 436/84 |

* cited by examiner

*Primary Examiner* — Maureen Wallenhorst
(74) *Attorney, Agent, or Firm* — Mossman, Kumar & Tyler, P.C.

(57) ABSTRACT

At least one pH-sensitive component may contact a refinery stream for measuring the pH of the refinery stream. A light from a light source may be emitted onto the pH-sensitive component, and a detector may detect a first luminescence or color change of chromophore measurement radiated from the pH-sensitive component. A first pH of the refinery stream may be determined from the first luminescence or color change of chromophore measurement.

20 Claims, No Drawings

METHODS OF MEASURING PH IN REFINERY STREAMS

CROSS-REFERENCE TO RELATED APPLICATION

This application claims the benefit of U.S. Provisional Patent Application No. 62/152,347 filed Apr. 24, 2015, incorporated herein by reference in its entirety.

TECHNICAL FIELD

The present invention relates to luminescence or color change of chromophore techniques for detecting pH in a refinery stream with a pH-sensitive component.

BACKGROUND

Converting oxygenates into light olefins is referred to as the oxygenate-to-olefin process. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. Non-limiting examples of olefins may be or include ethylene, propylene, and the like. Olefins are important petrochemicals used to make plastics or other chemicals, such as vinyl chloride, ethylene oxide, ethylbenzene, alcohols (with more carbon atoms than methanol and ethanol), acrylonitrile, propylene oxide, and the like.

There are numerous technologies available for producing oxygenate(s), including fermentation or reaction of synthesis gas derived from natural gas, petroleum liquids, carbonaceous materials including coal, recycled plastics, municipal waste, or any other organic material. To produce methanol, a combustion reaction of natural gas, mostly methane, and an oxygen source having hydrogen, carbon monoxide and/or carbon dioxide produces synthesis gas. Synthesis gas production processes are well known, and include conventional steam reforming, autothermal reforming or a combination thereof. The synthesis gas may then be converted into methanol, for use in the oxygenate-to-olefin process.

The oxygenate-to-olefins reaction is highly exothermic and may have a large amount of water. The effluent stream derived from an oxygenate-to-olefin process may include as much as one half of the total weight of the effluent stream as water. Consequently, the water must be removed by condensation in a quench device or a quench tower to isolate the olefin product. The stream is considered an effluent stream from the point the effluent stream exits an oxygenate-to-olefin reactor to the point the gaseous output stream is quenched; quenching the effluent stream produces a quenched effluent stream.

As used herein, "quench device", also known as a "quench tower", is a device for introducing a sufficient quantity of liquid quench medium to a gaseous effluent stream where the quench medium may condense at least a portion of the material in the effluent stream. A quench tower is a type of quench device having more than one quench stage. A "quench medium" is defined as a liquid that contacts the effluent stream to cool the effluent stream to the condensation temperature of water.

Generally, the step of quenching the effluent stream forms a quenched effluent stream and a liquid fraction or quench bottoms stream. As used herein, the terms, "liquid fraction" and "quench bottoms stream" are used interchangeably and refer to the portion of the effluent stream and quench medium that is liquid under quench conditions and includes all streams that contain the condensed portion of the effluent stream and fractions of the condensed effluent stream. The term "quenched effluent stream" refers to the portion of the effluent stream that is predominantly gaseous after at least one stage of quenching. Water from the quench bottoms stream may be treated or processed to remove the entrained hydrocarbons (e.g. quench oil, pyrolysis, gasoline, etc.) and potential coke fines that may foul heat exchangers and boilers, lead to poor separation in stripping units, increase energy consumption, and the like.

After treatment to the water, the water may be fed into a dilution steam system where steam may be added to the quenched effluent stream to reduce the partial pressure of hydrogen and shift the equilibrium toward a higher olefin yield. Dilution steam condensate is defined herein as the water condensed from a quench device prior to being treated for use in a dilution steam system, which is different from a dilution steam, i.e. water condensed from the quench device that has been treated for use in a dilution steam system. The refinery stream passes through the dilution steam system and eventually into the distillation tower.

The refinery stream enters the distillation tower as a vapor. As the vapor rises through the distillation tower, the vapor begins to cool. When a substance within the vapor reaches a height within the distillation tower where the temperature of the distillation tower is equal to the substance's boiling point, the substance will condense to form a liquid. The substance with the lowest boiling point will condense at the highest point in the tower, and substances with higher boiling points will condense lower in the tower. Trays within the distillation tower collect the liquid fractions, and the liquid fractions are passed to condensers, which cool the liquid fractions further.

The quench medium, the effluent stream, dilution condensate, dilution steam, and/or the distillation vapor often contain byproducts including oxygenate byproducts, such as carbon dioxide, organic acids, aldehydes, and/or ketones. Furthermore, depending upon operating conditions, unreacted oxygenates may be present in the effluent stream of the oxygenate-to-olefin reaction.

Neutralizing additives may contact the quench medium, the effluent stream, and/or dilution steam to alter the pH thereof. Measuring the pH of the quench medium, effluent stream, and/or dilution steam has been difficult because the electrodes are typically glass and foul quickly. In addition, the reference junction of pH electrodes and the internal filling solution may also become contaminated.

It would be desirable if alternative methods of measuring the pH of refinery streams were devised to alleviate some of these problems.

SUMMARY

There is provided, in one form, a method for measuring pH in a refinery stream by contacting the refinery stream with an apparatus comprising a pH-sensitive component, emitting a light from a light source onto the pH-sensitive component, detecting a first luminescence or color change of chromophore measurement radiated from the pH-sensitive component with a detector, and determining a first pH of the refinery stream from the first luminescence or color change of chromophore measurement.

In an alternative non-limiting embodiment of the method, the pH may be measured by contacting the refinery stream with a pH probe having a pH-sensitive component and a light source. A light may be emitted from the light source onto the pH-sensitive component, and a first measurement radiated from the pH-sensitive component may be detected with a detector. A first pH of the refinery stream may be determined from the first luminescence or color change of chromophore measurement. Optionally, the light may be emitted through the refinery stream onto the pH-sensitive component.

The pH-sensitive component provides a quicker and less expensive mechanism to determine the pH of a refinery stream.

DETAILED DESCRIPTION

It has been discovered that pH of a refinery stream may be measured by contacting a refinery fluid or refinery stream with an apparatus comprising a pH-sensitive component. A light source may emit a light onto the pH-sensitive component, and a detector may detect an indicator, including but not necessarily limited to, a first luminescence or a color change of chromophore measurement from the pH-sensitive component. In a non-limiting embodiment, the light source may be emitted through the refinery fluid. In a non-limiting embodiment, the first luminescence or color change of chromophore measurement may be detected through the refinery fluid; e.g. through the refinery fluid onto the pH-sensitive component in one non-limiting embodiment.

A first pH of the refinery stream may be determined from the first luminescence or color change of chromophore measurement of the pH-sensitive component. Multiple luminescence or color change of chromophore measurements may be obtained in this manner to obtain the pH of the refinery stream over a period of time. Said differently, "first pH" is used herein only to differentiate the pH of a refinery stream that has not been altered based on the methods discussed herein.

By using luminescence or color change of chromophore measurements to quantify the pH of the refinery fluid or stream, rapidly time-varying signals may be measured. The measurements may also be taken on-line or offline, and even at a remote location. The pH-sensitive component may be introduced into a sample extracted from the process, into a slip stream separate from the actual process stream, or directly into the process stream, and the like.

The apparatus may be or include a pH probe, a pH cuvette, a pH patch, and combinations thereof. A pH probe may include a visible light source, a spectrometer, and software to convert a luminescence or color change of chromophore measurement into a pH value. In a non-limiting embodiment, a spectrometer waveguide may have a pH patch applied to the end of the spectrometer waveguide to transform the spectrometer into a pH probe; with the use of this probe, an external light source would also need to be used. A pH cuvette may be a cuvette with a pH patch attached thereon. The refinery fluid may be placed into the cuvette, and the cuvette may be placed into a spectrometer for measuring the luminescence or color change of chromophore measurement(s) thereof. The pH patch is the simplest of the apparatus embodiments, and may have an adhesive thereon so the pH patch can adhere to a surface for contacting the refinery fluid. A spectrometer probe may be used in conjunction with the probe to measure the luminescence or color change of chromophore values of the refinery fluid in contact with the pH patch.

In the instance that the light source and/or the detector are external to the apparatus, the distance from the light source to the pH sensitive component may range from about 0.1 mm independently to about 100 mm, or from about 0.05 mm independently to about 50 mm. The distance from the detector to the pH sensitive component may range from about 0.1 mm independently to about 100 mm, or from about 0.05 mm independently to about 50 mm.

All of the apparatuses include a pH sensor component. In a non-limiting embodiment, the pH sensitive component may be a pH-sensitive chemical and/or dye used in the pH paper that changes color upon contact with the refinery fluid. The pH-sensitive component may be or include at least one pH sensitive chromophore in a non-limiting embodiment. pH sensitive chromophores have been used to facilitate sensing. As used herein, a "pH sensitive chromophore" is a chemical species that reacts to the presence of a substance to produce an optical result, e.g. a fluorophore. Another type of pH sensitive chromophore changes color in accordance with changes in an amount of a particular substance. Suitable pH sensitive chromophores include but are not necessarily limited to, litmus derivatives, phenolphthalein derivatives, and phenol red derivatives and combinations thereof. Specific examples of suitable pH sensitive chromophores include but are not necessarily limited to, LYSOSENSOR™ Blue DND-167; LYSOSENSOR™ Green DND-153; LYSOSENSOR™ Green DND-189; LYSOSENSOR™ Yellow/Blue DND-160; 2',7'-bis-(2-carboxyethyl)-5-(and-6-carboxyfluorescein (BCECF acid); carboxyfluorescein (5-(and 6-)carboxyfluorescein, succinimidyl ester); 6-JOE (6-carboxy-4',5'-dichloro-2',7'-dimethoxyfluorescein, succinimidyl ester); naphthofluorescein (5-(and 6-)carboxynaphthofluorescein, succinimidyl ester); Oregon Green 488 carboxylic acid, succinimidyl ester; Oregon Green 514 carboxylic acid, succinimidyl ester; pHrodo succinimidyl ester; SNARF-1 carboxylic acid, acetate, succinimidyl ester; 5-(and 6-)carboxy SNARF-1; SNARF-4F carboxylic acid; SNARF-5F carboxylic acid; all available from THERMOFISHER Scientific.

The pH-sensitive component, e.g. a pH sensitive chromophore in a non-limiting embodiment, may be trapped in a solid substance and deposited as a thin layer or a membrane onto or within an apparatus. The pH sensitive component may be used with a light source and a detector. The pH sensitive component, light source, and the detector may all be included within the apparatus. Alternatively, the light source and/or detector may be external to the pH sensitive component.

The pH-sensitive component within the apparatus may contact the refinery fluid or stream to interact with the hydrogen ions, hydronium ions, other acid species, and the like within the refinery fluid sample or refinery fluid stream, which results in a change in luminescence or color change of chromophore properties. An optical detector may detect the change in luminescence or color change of chromophore properties. The optical detector may be a single photodetector with an optical filter, a spectrometer, or any optical detection system capable of measuring light intensity or the change in light intensity over time. These optical properties of chemical sensor compositions typically involve changes in colors or in color intensities, fluorescence intensity, or fluorescence lifetime.

To at least partially clean the apparatus, any remaining refinery stream, which in one non-limiting embodiment may be called "excess refinery fluid", may be at least partially removed from the apparatus after each luminescence or color change of chromophore measurement has been detected by a technique, such as but not limited to, vacuuming the apparatus, contacting the apparatus with compressed air, and combinations thereof. The apparatus may then be used to detect at least a second luminescence or color change of chromophore measurement from the refinery fluid. Of course, the apparatus may be used to detect at least a second luminescence or color change of chromophore measurement in the absence of removing any excess refinery stream therefrom; however, the measurements obtained from the apparatus may become less accurate with an increased usage of the apparatus in the absence of any cleaning.

In another non-limiting embodiment, the apparatus may allow for miniaturization and remote sensing of streams. The pH-sensitive component (e.g. pH sensitive chromophore) may be immobilized, via mechanical or chemical means, to one end of an optical fiber in the instance a fiber optic probe is used. A fiber coupler (Y-shaped fiber) or a beam splitter may be attached to the opposite end of the fiber. Incident excitation light may be coupled into one leg of the fiber by a filter and a lens. Excitation light may be carried through the fiber to the distal end where the pH sensitive chromophore or other pH-sensitive component may be immobilized to the tip.

In the non-limiting instance of a pH sensitive probe, excitation of the pH sensitive component may uniformly radiate the light, and some of the light may be recaptured by the fiber tip and propagated back through the fiber to the junction or "coupler". At the junction, a substantial portion (typically half) of the light may be conveyed back to the emitter or point of origin thereby unavailable for signal detection. To offset the inefficiencies of the system, lasers may be used to raise the input power, and highly sensitive photomultiplier tubes may be used as detectors. The other half of the fluorescence may travel along the other leg of the fiber to the detector to be recorded.

In a non-limiting embodiment, the pH-sensitive component may be introduced into the refinery stream at a location, such as but not limited to, a dilution steam generator, a distillation tower, a process water stripper, a quench water tower, an oil/water separator, and combinations thereof. In a non-limiting embodiment, the first pH of the refinery stream may be altered based on the pH determination.

In one non-limiting embodiment, the pH-sensitive component may be coated onto the apparatus, such as but not limited to, a probe, a cuvette, a patch, and combinations thereof by a sol-gel technique to encapsulate the pH-sensitive component sensitive onto the apparatus. To coat the pH-sensitive component onto the apparatus with this technique, a fluorinated sol gel precursor [(3,3,3-trifluoropropyl) triethoxysiloxane] may be added to methyltrimethoxysilane (MTMS) for fabricating a multicomponent sol gel medium, in one non-limiting embodiment. Other fluorinated siloxanes precursors may be used, such as but not limited to, (tridecafluoro-1,1,2,2-tetrahydroocyyl)triethoxysilane and (tridecafluoro-1,1,2,2-tetrahydrooctyl)trimethoxysilane.

The sol gel may be coated onto the apparatus or other plastic or glass surfaces. To thermally and/or optically cure the coating, the coating may be mixed for three (3) hours, then stored overnight, air aged after coating for one (1) week and then thermal aged at fifty (50) degrees Centigrade overnight. Non-limiting examples of apparatuses that may be used to measure pH in refinery streams hydrocarbon are the transmissive pH probes and/or the reflective pH patches supplied by OCEAN OPTICS™.

The pH measurable by the apparatus may range from about 4 independently to about 9.5. The pH of the refinery stream may vary depending on the specific type of refinery stream in a non-limiting embodiment, such as but not limited to from about 5.5 independently to about 9.5. The pH of a fluid within a quench water tower may range from about 5.5 to about 7.5. The pH of a fluid within a process water stripper may range from about 7.8 to about 8.8. The pH of a fluid within a dilution steam generator blowdown may range from about 8.5 to about 9.5. The pH of a fluid during a distillation tower overhead knockout process may range from about 5.5 to about 8.5. The pH of the refinery stream may be determined at any of these locations. If the first pH is outside of a desired pH range depending on the location of the refinery stream and/or the type of refinery stream, the pH may be altered, i.e. increased or decreased using chemicals and/or processes known to those skilled in the art; including, but not necessarily limited to, adding one or more acid and/or adding one or more base. In a non-limiting embodiment, the method of measuring the pH of the refinery stream may occur in an amount of time that ranging from about 10 seconds to about one hour, alternatively from about 1 minute independently to about 10 minutes.

The light from the light source may have a wavelength ranging from about 200 nm independently to about 800 nm, or from about 300 nm independently to about 950 nm. The light source may be or include, but is not limited to, a light emitting diode, a laser light, and combinations thereof.

In another non-limiting embodiment, the apparatus may also include a mechanism for detecting a temperature of the refinery stream. The mechanism may be or include a temperature sensor, thermometer, thermocouple, or like device in a non-limiting embodiment.

In a non-limiting embodiment, the luminescence or color change of chromophore measurement(s) may be absorbance measurement(s), i.e. where the absorbance of the light radiated from the pH-sensitive component is measured. The pH of the refinery stream may be determined from the absorbance measurement from the pH-sensitive component after a light has been emitted thereon with the following formula:

$$pH = pK_a + slope \times \log(Abs_{sample}/Abs_{pH11} - Abs_{sample})$$

where:
$pK_a$ is the acid dissociation constant for the refinery stream;
$pK_a = -\log_{10} K_a$ where $K_a = ([A-][H+])/[HA]$;
slope is sensitivity of the measurement;
$Abs_{sample}$ is the absorbance measurement of the sample; and
$Abs_{pH11}$ is the absorbance measurement of the sample at a pH of 11.

The refinery stream may be or include an aqueous-based refinery stream, a hydrocarbon-based refinery stream, and combinations thereof. Alternatively, the refinery stream may be or include, but is not limited to, a quench medium, an effluent stream, a dilution condensate, a dilution steam, a distillation vapor, a mixed $C_4$ hydrocarbon stream, a light ends hydrocarbon stream, a styrene hydrocarbon stream, cracked gas distillates, hydrotreater feeds, kerosene, a pyrolysis gas stream, and combinations thereof.

A non-limiting example of a "mixed $C_4$ hydrocarbon stream" is a crude butadiene stream, or a mixed $C_4$ hydrocarbon stream may be one produced from ethylene crackers and contains anywhere from 30 to 80% of 1-3 butadiene, and the like. During the storage and/or transportation of these streams, butadiene may react to form polymers, which can foul flow meters and the transferring pipelines. In addition, polyperoxides may also build up while in storage causing an explosion risk.

"Light ends" are defined herein to be or include the lower-boiling components of a mixture of hydrocarbons, such as those evaporated or distilled off easily in comparison to the bulk of the mixture; e.g. "light ends" may be C6 and lighter. Non-limiting examples of "light ends" may be or include, but are not limited to, distillates, such as a straight run distillate, a cracked distillate, and the like.

With respect to the color change of chromophore embodiment, suitable dyes to be injected into the refinery stream include, but are not necessarily limited to, litmus derivatives, phenolphthalein derivatives and phenol red derivatives, LYSOSENSOR™ probes available from THERMO-FISHER Scientific, and the like and combinations thereof. The amount of dye injected into the refinery stream to measure the pH in the stream ranges from about 0.01 wt % independently to about 20 wt %; alternatively from about 0.04 wt % independently to about 40 wt %. Non-limiting examples of a change in dye color include, but are not limited to blue to red, blue to green, orange to red, orange to green, and the like.

As used herein with respect to a range, "independently" means that any lower threshold may be used together with any upper threshold to give a suitable alternative range.

In the foregoing specification, the invention has been described with reference to specific embodiments thereof, and has been described as effective in providing methods for measuring pH in a refinery stream. However, it will be evident that various modifications and changes can be made thereto without departing from the broader scope of the invention as set forth in the appended claims. Accordingly, the specification is to be regarded in an illustrative rather than a restrictive sense. For example, specific refinery streams or fluids, refinery stream apparatus, pH-sensitive components, pH sensitive chromophores, light wavelengths, dyes, salts, pHs or pH ranges, temperature sensors, and/or acid species falling within the claimed parameters, but not specifically identified or tried in a particular method, are expected to be within the scope of this invention.

The present invention may suitably comprise, consist or consist essentially of the elements disclosed and may be practiced in the absence of an element not disclosed. For instance, the method for measuring pH in a refinery stream may consist of or consist essentially of contacting a refinery stream with an apparatus comprising a pH sensitive component, emitting a light from a light source onto the pH-sensitive component, detecting a first luminescence or color change of chromophore under acidic condition measurement radiated from the pH-sensitive component with a detector, and determining a first pH of the refinery stream from the first luminescence or color change of chromophore measurement.

The words "comprising" and "comprises" as used throughout the claims, are to be interpreted to mean "including but not limited to" and "includes but not limited to", respectively.

As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, the term "and/or" includes any and all combinations of one or more of the associated listed items.

As used herein, relational terms, such as "first," "second," "top," "bottom," "upper," "lower," "over," "under," etc., are used for clarity and convenience in understanding the disclosure and accompanying drawings and do not connote or depend on any specific preference, orientation, or order, except where the context clearly indicates otherwise.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" in reference to a given parameter is inclusive of the stated value and has the meaning dictated by the context (e.g., it includes the degree of error associated with measurement of the given parameter).

What is claimed is:

1. A method for measuring pH in a refinery stream; wherein the method comprises:
    contacting a refinery stream with an apparatus comprising a pH sensitive component deposited as a thin layer or membrane onto or within the apparatus, where the contacting further comprises introducing the pH sensitive component directly into the refinery stream or into a slip stream from the refinery stream;
    emitting a light from a light source through the refinery stream onto the pH-sensitive component;
    detecting a first luminescence measurement or color change of chromophore measurement radiated from the pH-sensitive component through the refinery stream with a detector; and
    determining a first pH of the refinery stream from the first luminescence measurement or the color change of chromophore measurement.

2. The method of claim 1, wherein the apparatus is present in the refinery stream at a location selected from the group consisting of a dilution steam generator, a distillation tower, a process water stripper, a quench water tower, an oil/water separator, and combinations thereof.

3. The method of claim 1 further comprising altering the pH of the refinery stream when the first pH is outside of a pH range of from about 4.0 to about 9.5.

4. The method of claim 1, wherein the method occurs in an amount of time that is one minute or less.

5. The method of claim 1, wherein the light comprises a wavelength ranging from about 200 nm to about 950 nm.

6. The method of claim 1, wherein the apparatus further comprises a temperature sensor, and wherein the method further comprises detecting a temperature of the refinery stream with the apparatus.

7. The method of claim 1, wherein the apparatus is selected from the group consisting of a probe, a cuvette, a patch, and combinations thereof.

8. The method of claim 1, wherein the first luminescence measurement is an absorbance measurement, and wherein the first pH of the refinery stream is determined from the absorbance measurement with the following formula:

$$pH = pK_a + slope \times \log(Abs_{sample}/Abs_{pH11} - Abs_{sample})$$

where:
  $pK_a$ is the acid dissociation constant for the refinery stream; $pK_a=-\log_{10}K_a$ where $K_a=([A-][H+])/[HA]$;
  slope is sensitivity of the measurement;
  $Abs_{sample}$ is the absorbance measurement of the sample; and
  $Abs_{pH11}$ is the absorbance measurement of the sample at a pH of 11.

9. The method of claim 1, wherein the refinery stream is selected from the group consisting of an aqueous-based refinery stream, a hydrocarbon-based refinery stream, and combinations thereof.

10. The method of claim 1, wherein the refinery stream is selected from the group consisting of a quench medium, an effluent stream, a dilution condensate, a dilution steam, a distillation vapor, a mixed $C_4$ hydrocarbon stream, a light ends hydrocarbon stream, a styrene hydrocarbon stream, cracked gas distillates, hydrotreater feeds, kerosene, a pyrolysis gas stream, and combinations thereof.

11. The method of claim 1 where:
  a distance from the light source to the pH sensitive component ranges from about 0.1 to about 100 mm; and
  a distance from the detector to the pH sensitive component ranges from about 0.1 to about 100 mm.

12. A method for measuring pH in a refinery stream;
  wherein the method comprises:
    contacting a refinery stream with a pH probe comprising a pH-sensitive component deposited as a thin layer or membrane onto or within the pH probe, and a light source where the contacting further comprises introducing the pH sensitive component directly into the refinery stream or into a slip stream from the refinery stream;
    emitting a light from the light source onto the pH-sensitive component;
    detecting a first luminescence measurement radiated from the pH-sensitive component through the refinery stream with a detector; and
    determining a first pH of the refinery stream from the first luminescence measurement.

13. The method of claim 12, wherein the pH probe is attachable to the detector.

14. The method of claim 12, wherein the pH probe is present in the refinery stream at a location selected from the group consisting of a process stripper, a dilution steam generator, a distillation tower, a quench water tower, an oil/water separator, and combinations thereof.

15. The method of claim 14, further comprising removing excess refinery fluid from the pH probe after the first luminescence measurement has been detected by a technique selected from the group consisting of vacuuming the pH probe, contacting the pH probe with compressed air, and combinations thereof.

16. The method of claim 15, further comprising detecting at least a second luminescence measurement from the refinery stream with the pH probe to determine a second pH of the refinery stream from the second luminescence measurement.

17. A method for measuring pH in a refinery stream;
  wherein the method comprises:
    contacting a refinery stream with a pH patch comprising a pH-sensitive component deposited as a thin layer or membrane onto or within the pH patch, where the contacting further comprises introducing the pH sensitive component directly into the refinery stream or into a slip stream from the refinery stream;
    emitting light from a light source through the refinery stream onto the pH-sensitive component; and
    detecting a first luminescence measurement radiated from the pH-sensitive component through the refinery stream with a detector;
    determining a first pH of the refinery stream from the first luminescence measurement; and
    altering the pH of the refinery stream.

18. The method of claim 17, wherein the refinery stream is selected from the group consisting of a quench medium, an effluent stream, a dilution condensate, a dilution steam, a distillation vapor, a mixed $C_4$ hydrocarbon stream, a light ends hydrocarbon stream, a styrene hydrocarbon stream, cracked gas distillates, hydrotreater feeds, kerosene, a pyrolysis gas stream, and combinations thereof.

19. The method of claim 17, wherein the pH patch contacts the refinery stream at a location selected from the group consisting of a dilution steam generator, a distillation tower, a process water stripper, a quench water tower, an oil/water separator, and combinations thereof.

20. The method of claim 17, wherein the altering the pH of the refinery stream occurs when the first pH is outside of a pH range from about 4.0 to about 9.5.

* * * * *